US011437055B2

United States Patent
Hansen

(10) Patent No.: US 11,437,055 B2
(45) Date of Patent: Sep. 6, 2022

(54) METHOD AND DEVICE FOR INCREASING MUSICAL SENSITIVITY

(71) Applicant: FEELBELT GMBH, Potsdam (DE)

(72) Inventor: Jens Hansen, Berlin (DE)

(73) Assignee: FEELBELT GMBH, Potsdam (DE)

( * ) Notice: Subject to any disclaimer, the term of this patent is extended or adjusted under 35 U.S.C. 154(b) by 0 days.

(21) Appl. No.: 17/156,553

(22) Filed: Jan. 23, 2021

(65) Prior Publication Data

US 2021/0174822 A1    Jun. 10, 2021

Related U.S. Application Data

(63) Continuation of application No. PCT/DE2019/100675, filed on Jul. 24, 2019.

(30) Foreign Application Priority Data

Jul. 24, 2018    (DE) .......................... 102018006210.5

(51) Int. Cl.
| | | |
|---|---|---|
| *G10L 21/06* | (2013.01) | |
| *A61F 11/04* | (2006.01) | |
| *G09B 21/00* | (2006.01) | |

(52) U.S. Cl.
CPC .............. *G10L 21/06* (2013.01); *A61F 11/04* (2013.01); *G09B 21/009* (2013.01)

(58) Field of Classification Search
CPC ................................ G10L 21/06; A61F 11/04
USPC ........................................................ 704/271
See application file for complete search history.

(56) References Cited

U.S. PATENT DOCUMENTS

| | | | |
|---|---|---|---|
| 4,167,189 A | 9/1979 | Tachi et al. | |
| 4,250,637 A | 2/1981 | Scott | |
| 4,390,756 A | 6/1983 | Hoffman et al. | |
| 5,035,242 A * | 7/1991 | Franklin | .............. G09B 21/009 607/108 |
| 8,167,826 B2 * | 5/2012 | Oohashi | ................. G10K 15/02 601/2 |
| 10,264,339 B2 | 4/2019 | Schwartz | |

(Continued)

FOREIGN PATENT DOCUMENTS

| | | |
|---|---|---|
| DE | 3924708 | 10/1991 |
| WO | 9633481 | 10/1996 |

(Continued)

OTHER PUBLICATIONS

WIPO, Translation of International Search Report in corresponding PCT application PCT/DE2019/100675, dated Sep. 27, 2019.

(Continued)

*Primary Examiner* — Susan I McFadden
(74) *Attorney, Agent, or Firm* — Ryan Alley IP

(57) ABSTRACT

A method and a device for increasing the perception of acoustic events, particularly for increasing musical sensitivity. As high a correlation as possible between heard and felt perceptions can be achieved by the conversion of the musical signal into vibrations on the skin, the local impact distribution of the filtered musical signals, the emphasis of the dominant musical signals by expanding the extent of the impact, the transfer of the signal portions in the non-feelable range into the feelable range, and the variable base spectrum adapting to the current musical spectrum.

21 Claims, 2 Drawing Sheets

(56) References Cited

U.S. PATENT DOCUMENTS

2007/0242040 A1 10/2007 Ulrich et al.
2008/0159569 A1* 7/2008 Hansen ................ G09B 21/009
381/151

FOREIGN PATENT DOCUMENTS

WO    2006092136    9/2006
WO    2010020201    2/2010

OTHER PUBLICATIONS

Karam et al, "The Emoti-Chair: An interactive tactile music exhibit" Apr. 10, 2010.

* cited by examiner

METHOD AND DEVICE FOR INCREASING MUSICAL SENSITIVITY

RELATED APPLICATIONS

This application claims priority under 35 U.S.C. § 120 to, and is a continuation of, co-pending International Application PCT/DE2019/100675, filed Jul. 24, 2019 and designating the US, which claims priority to DE Application 10 2018 006 210.5, filed Jul. 24, 2018, such DE Application also being claimed priority to under 35 U.S.C. § 119. These DE and International applications are incorporated by reference herein in their entireties.

BACKGROUND

Field

The invention relates to a method and a device for increasing perception of acoustic events or signals, in particular of music, in that vibrations are preferably derived therefrom and transmitted onto the skin.

From WO 2006/092136 A2, a method and a device are known for the sensitive detection of audio events in order to achieve sensation or feeling states of the living skin. In this case, only the sensible (feelable) frequency range of the audio events is converted into vibrations by spectrally splitting the audio event and essentially using the currently dominant spectral range for actuating the vibration transmitters, with the number of vibration transmitters depending on the frequency position of said spectral ranges. However, it is not disclosed how this derivation is carried out in order to achieve a correlation between heard and felt audio events, in particular music. Furthermore, the switching scheme for the vibration transmitters is based on the amplitudes of the spectra. However, they are not decisive for the vibration strength of the vibration transmitters.

Based on this, the objective of WO 2010/020 201 A1 was to ensure that music content above the sensible frequency range, i.e. approximately above 600 Hertz, are also detected. However, this cannot be achieved with the described realization because the amplitude of a spectrum does not correspond to the amplitude of the temporal signal with this spectrum.

In methods in which audio events for the hearing impaired are converted into learned sensory perception patterns, acoustic signals defined in terms of content are transmitted to deaf persons in a sensory manner, so that they can be understood by said persons. Such solutions are based on a previous learning process and are known, for example, from U.S. Pat. Nos. 5,035,242, 4,167,189, EP 0 766 218 A1, U.S. Pat. Nos. 4,250,637, 4,390,756, or DE 39 24 708 A1.

SUMMARY

The problem addressed by the invention is that of increasing the perception of acoustic events, in particular musical sensitivity. In particular, the vibrations acting on the skin and the selection of the impact locations, which should have a high sensitivity to external influences, are intended to be optimally adapted with regard to the correlation to the music and the ability of the skin to differentiate and perceive.

A correlation of heard and felt perceptions is important because otherwise both impressions would not be considered as belonging together, i.e. they would be considered as extraneous impressions, and an increase in perception, e.g. an intensification of the musical experience, would not be present.

In particular, the second perception, i.e. the tactile perception through vibrations, should have a direct effect on the listener, i.e. touch said listener, so to speak, and reflect the perception heard therein, so to speak, in order to effect an increase in the perception, in particular the sensitivity, which may be denoted also as emotionality.

The problem is solved by a method and a device having the features of the independent claims. Advantageous embodiments are the subject matter of the dependent claims.

For a better understanding, some of the terms used shall be explained in advance.

Base spectrum is a frequency spectrum determined from the frequency spectrum of an acoustic event, in particular a selected portion of the entire frequency spectrum. It can refer to a mean selected frequency spectrum which is adapted on the basis of the currently available frequency spectrum of the acoustic event, e.g. music currently being heard, by making it narrower or wider. In particular, base spectrum thus refers to the spectral range in which the essential contents of an acoustic signal lie.

Partial spectra are spectral ranges into which the base spectrum can be divided. In particular, the base spectrum is divided into partial spectra preferably such that the partial spectra in total form the base spectrum. The number of partial spectra can be specified, and in particular can correspond to the number of vibration transmitters. The partial spectra can have the same or different widths.

Amplitude refers to the mean level of the temporal profile of a spectral range.

Control voltages are the voltages for actuating the vibration transmitters and are derived from the frequency range of at least one of the partial spectra.

Acoustic events comprise any type of audio event of which the perception is supposed to be increased during the event by generating vibrations, the aim of the perception increase essentially being the increase of the emotional effect intended with a piece of music. In addition, an increase in music recognizability can also be effected, for example, in the case of loud background noises or quiet music. Acoustic events also comprise voices, sounds, noises or tones (e.g. audio for pictorial/video material, such as audio for a film, sounds of a video game, etc.) if the term "music" is used.

According to one aspect of the invention, a method for increasing the perception of acoustic events, in particular for increasing musical sensitivity, is provided. For this purpose, vibrations derived from an acoustic event and correlating with the acoustic event are transmitted onto the skin of a person by means of vibration transmitters, wherein the vibration transmitters are spatially distributed on the skin at positions in a predetermined arrangement. By means of a controller, to which an input signal reproducing the acoustic event is fed, control voltages are determined and the vibration transmitters are each actuated with one of the determined control voltages in order to generate a vibration that is sensible (feelable) on the skin.

A base spectrum is determined from the frequency spectrum of the acoustic event, in particular is selected as a portion of the frequency spectrum, wherein the base spectrum is divided into partial spectra which each comprise a frequency range of the base spectrum. The control voltages are then each derived from the frequency range of an assigned partial spectrum (or possibly a plurality of partial spectra). In this case, there is an assignment between the frequency positions of the control voltages and the positions of the vibration transmitters and/or between the partial spectra and the positions of the vibration transmitters.

A suitable determination of the base spectrum from the entire frequency spectrum of an acoustic event creates the basis for an increase in perception. The selection of the base spectrum can depend in particular on the type of acoustic event. For example, the base spectrum for bass-heavy music can be selected in a range of lower frequencies than for treble-heavy music. A suitable selection of the width of the base spectrum can also increase perception. For example, even in the case of acoustic events in which the main portion of the frequencies lies in a narrow range, a distribution across all vibration transmitters can be achieved by appropriately selecting the width of the base spectrum. Without the selection of such a base spectrum, for example, in the case of bass-heavy music, the vibration transmitters assigned to partial spectra with high frequencies would barely be excited to vibrate. In addition to the selection of the base spectrum, the perception is further increased by assigning the vibration transmitters, in particular with regard to their position within the arrangement, so that sounds of different frequencies can be perceived at different locations on the skin.

While the base spectrum can be predetermined or, for example, only determined once at the start, it is advantageous if the base spectrum is variable, i.e. it is continuously adapted in particular to the current acoustic event or adapted at least at predetermined intervals during the current acoustic event. By means of this "dynamic" adaptation of the base spectrum, an increased perception can be achieved at any time during the acoustic event.

In particular, determining the base spectrum can comprise an expansion and/or reduction of the width of the base spectrum while maintaining the number of partial spectra, wherein the width of the base spectrum is reduced if, within a time unit, a number of spectral components occurs in the frequency range of the acoustic event in the edge regions of the current base spectrum (i.e. within a specified distance from the relevant edge) which lies below a specified threshold value, in particular no spectral component, and wherein the width of the base spectrum is expanded if a spectral component which lies outside the selected base spectrum occurs in the frequency spectrum of the acoustic event.

According to a further aspect, a device for increasing the perception of acoustic events is provided which is configured to carry out the method described herein. The device has a plurality of vibration transmitters for transmitting vibrations onto the skin of a person and a controller connected to the vibration transmitters for actuating the vibration transmitters with a control voltage in order to generate the vibrations. The vibration transmitters are arranged at positions in a predetermined arrangement such that they can be spatially distributed on the skin of the person, wherein vibrations derived from an acoustic event and correlating with the acoustic event can be transmitted onto the skin of a person by means of the vibration transmitters. The controller is configured to receive an input signal belonging to the acoustic event, to determine control voltages and to actuate the vibration transmitters with one of the determined control voltages in order to generate a vibration that is sensible (feelable) on the skin.

The device can be designed, for example, as a belt to be worn around the hips or waist, as a band or as an item of clothing (e.g. as a vest or T-shirt), preferably such that, when used, the vibration transmitters can be placed on the skin in the area of the abdomen and the waist or hips of the person, which is particularly advantageous due to the proximity to the vegetative nervous system. In particular, the vibration transmitters can be arranged such that they come into contact with the skin of the person when said person wears the device or they can be arranged at least relative to the skin of the person such that a vibration can be transmitted onto the skin. For example, the vibration transmitters can be integrated into the device, for example covered by a layer of material, to increase wearing comfort.

According to a further aspect, a method for increasing musical sensitivity is provided in that vibrations derived from the audible music and correlating with the audible music are transmitted onto the skin by vibration transmitters, wherein the vibration transmitters are spatially distributed in a belt to be worn around the hips or waist and are actuated by musical signals filtered into different frequency ranges as control voltage, wherein it is provided that, starting from a mean spectral width of a base spectrum from the musical spectrum, wherein the base spectrum is divided into partial spectra, the width of the base spectrum is expanded while maintaining the number of partial spectra as soon as a spectral component of the current music occurs that lies outside the current base spectrum and/or the width of the base spectrum is reduced while maintaining the number of partial spectra if, within a time unit, no spectral component of the current music occurs in the outer ranges of the current base spectrum, wherein the vibration transmitters are actuated with the temporal profiles of the partial spectra, and wherein a computationally retrievable assignment scheme exists between the frequency position of the control voltages and the position of the vibration transmitters.

According to a preferred embodiment of the method described above, the number of vibration transmitters actuated by a control voltage depends on the amplitude ratio of the individual control voltages, wherein, in case of the same or substantially the same amplitude (i.e. up to a predetermined deviation) of the control voltages of all partial spectra, the control voltage is fed to the vibration transmitters in the sequence of their frequency position, and in the case of a dissimilarity or when a predetermined deviation of the amplitude of the control voltages of the partial spectra is reached, the dominant control voltage is provided for the vibration transmitter of said spectrum and for the vibration transmitters of partial spectra with a higher frequency position.

It can be provided that the control voltage which has the highest amplitude in the frequency position below the control voltage with the maximum value is also used to actuate one or more vibration transmitters which would otherwise be assigned to the frequency ranges between said two control voltages, and there is a corresponding assignment for the control voltages below the activated frequency range.

The extents of the impact of the filtered input signals in the sensible spectral range are thus expanded depending on the frequency position and the amplitude dominance.

Regardless of this assignment of the control voltages, it is advantageous for making the heard music sensible if at least one vibration transmitter is permanently actuated with the highest-frequency control voltage of the partial spectra.

The vibration transmitters are preferably arranged symmetrically and in pairs with respect to a center line of the arrangement of the vibration transmitters, in particular with regard to a distribution direction in which the arrangement extends, and are actuated in pairs or individually. For this purpose, the center line of the arrangement can correspond to the center line of the device, for example the center line of a belt. In this case, the vibration transmitters can be arranged in particular along a line. However, it is also conceivable that the vibration transmitters are spaced apart in the distribution direction, but do not lie on a row or line. It is equally possible to provide more than one row of vibration transmitters next to one another, with the same number or a different number of vibration transmitters per row. The vibration transmitters can also be arranged arbitrarily, as long as there is an assignment as described above. The frequency of the partial spectra preferably increases in the direction of the center line, e.g. of the belt. In other words, vibration transmitters that are closer to the center line are assigned to partial spectra in a higher frequency range, and are preferably excited to a higher frequency vibration with a higher frequency control voltage than vibration transmitters that are further away from the center line. Such actuation, in which in particular the highs are made sensible on the abdomen and the lows (basses) on the sides by corresponding vibrations, has proven to be advantageous for increasing the perception of an acoustic event, in particular the increase in musical sensitivity, due to the different sensitivities of the skin at different locations. Due to the proximity of the sensitive impacts in the waist region to the vegetative nervous system, they are perceived particularly sensitively.

In the case of the vibration transmitter which is permanently actuated with the highest-frequency control voltage of the partial spectra, the paired arrangement is preferably the vibration transmitter pair located immediately to the right and left of the center line.

The method also includes method steps with which musical phases in the non-sensible (non-feelable) frequency range, which clearly characterize the music, are made sensible. In other words, there can be ranges in the frequency spectrum of an acoustic event which are audible with regard to their frequency (or at least contribute to the auditory impression), but would not be sensible on the skin at this frequency.

For example, it can be provided that the amplitude of the control voltage in the highest, still sensible partial spectrum is increased; in other words, if signal portions of the input signal occur in a non-sensible partial spectrum, the amplitude of the control voltage in the highest, still sensible partial spectrum is increased.

Furthermore, beginning from a specific dominance of the musical phase in the non-sensible frequency range, the control voltage in the highest, still sensible partial spectrum can be fed to a plurality of vibration transmitters as control voltage. This would increase the extent of the impact of said musical phase.

A further embodiment provides that the amplitude profile of the input signal lying in the non-sensible frequency range is impressed as an amplitude profile on an oscillation voltage lying in the sensible frequency range and this is fed as control voltage to the vibration transmitters.

One advantageous embodiment of this amplitude profile transfer provides that the selection amplifier used to separate the non-sensible from the sensible frequency range has a dynamic operating point setting such that the rectified output signal of the amplifier is fed back to the amplifier input in phase opposition via a time delay stage, resulting in an amplification that depends on the rate of change of the musical signal lying in the non-sensible frequency range, and the amplitude profile of the output signal of the amplifier thus generated is impressed as an amplitude profile on the oscillator voltage lying in the sensible range, which is subsequently used as control voltage for the vibration transmitters.

The time delay of the feedback signal is dimensioned such that it does not follow relatively rapid increases in the musical signal, i.e. the full amplification is effective in such musical phases, but when the musical signal remains at the higher level, the amplification is reduced according to the time constant of the feedback signal due to its phase opposition, and the operating point is moved to the lower voltage range. The basic amplification then acts again on another rapid increase, wherein, due to the low output voltage, the amplified signal can take shape entirely in the upper voltage range.

With a constant operating point position, signal fluctuations above a specific base signal amplitude would not be detectable because they would lie outside the operating range, i.e. in the saturation range, of the amplifier. On the other hand, with reduced amplification, the control voltages for the vibration transmitters would be too low to be able to detect signal fluctuations sensitively.

Due to the variable operating point position, the basic amplification can be increased to approximately five times the value, so that even small amplitude fluctuations of relatively high signals are detected sensitively.

In a further embodiment, it can be provided that, in the case of signal portions of the music in a non-sensible partial spectrum, said frequency range is detected in its entirety via one or more, preferably at least two, filter stages. This takes into account the fact that in music—in contrast to speech—several signal sources generate the sound. By detecting the frequency range via only one filter stage, the modulation contents of the individual sources can falsify one another, for example, through the formation of interference. If a plurality of filters is used, the circuit approximates the selection ability of the auditory system, resulting in a stronger correlation between heard and felt perceptions.

The assignment scheme of the control voltages to the vibration transmitters can be carried out with at least two filter stages such that the vibration transmitters located closer to the center line are actuated with the control voltages derived from the higher-frequency signal, and the vibration transmitters located further away from the center line are actuated with the control voltages derived from the low-frequency signal.

In the case of an amplitude dominance of a control voltage, it has proven to be advantageous if further (or at least one further) vibration transmitters are actuated with said voltage, in particular vibration transmitters which are adjacent to the actually assigned vibration transmitter.

In the case of pieces of music with a limited spectral range, it can be provided that the division of the frequency ranges for the control voltages is spread according to the total width of the music. This means that the width of the spectral ranges, which should be one octave wide, becomes smaller.

Another advantageous embodiment provides that control commands can be transmitted via a user interface, preferably via software such as an app, in particular to the digital circuit for implementing the switching scheme and/or for changing the assignment or switching matrix for the vibration transmitters.

As described above, a corresponding device, such as a belt, is provided with the vibration transmitters in order to implement the method described above. According to a further aspect, a device for increasing musical sensitivity can be provided, in that vibrations derived from the audible music and correlating with the audible music are transmitted onto the skin by vibration transmitters, wherein the vibration transmitters are arranged in a belt to be worn around the waist and are actuated by musical signals filtered into different partial spectra in the form of a control voltage. An electronic system is provided which, in terms of circuitry, consists of components coupled to one another, namely a music recording component, a circuit for deriving the base spectrum, controllable filter circuits with a circuit for adapting the filtered signals, circuits for amplitude detection, comparator circuits, a digital circuit for implementing the switching scheme, controllable amplifiers, a switching matrix, and the vibration transmitters.

It goes without saying that, instead of the analog circuit described, a digital circuit (e.g. a microcontroller) and/or software can advantageously be used as the controller. It receives a digital input signal, carries out the steps described for determining the control voltages and initiates the actuation of the vibration transmitters with the relevant control voltage.

The controller or electronic system is preferably integrated in the device and has at least one interface for receiving the input signal, for example an interface to a signal transmitter in/or on the music recording component. It can preferably be provided that the interface is wireless, for example Bluetooth, which receives the input signal from an output device. It goes without saying that the interface can also be wired. It can also be provided that the input signal is output or relayed via an interface, in particular to a device for playback, such as headphones or loudspeakers. In order to increase perception, the transmissions of the signals should not result in a time delay between the acoustic event heard and its conversion into vibrations.

Furthermore, the device advantageously has an energy storage means, such as a rechargeable battery, which is coupled to the controller in order to supply it with electric energy. This has the advantage that the device can be used independently even if the musical signals are transmitted by radio. The user is thus location-independent.

The vibration transmitters are preferably arranged on the inside of the device, for example arranged on the inside on or in the belt, so that, as described above, they can transmit the vibrations onto the skin.

By interacting with the digital circuit for implementing the switching scheme, at least the following actuations of the vibration transmitters can be carried out in combination or individually by the switching matrix, namely in that, in case of the same amplitude of the control voltage of all partial spectra, the control voltage is fed to the vibration transmitters in the sequence of their frequency position, in that, in the case of a dissimilarity of the amplitude of the control voltages of the partial spectra, the dominant control voltage is provided for the vibration transmitter of said partial spectrum and for one or more vibration transmitters of the partial spectra with a higher frequency position, in that at least one vibration transmitter is permanently actuated with the highest-frequency control voltage of the partial spectra, in that the control voltage which has the highest amplitude in the frequency position below the control voltage with the maximum value is also used to actuate one or more vibration transmitters which lie between said two control voltages, and in that there is a corresponding assignment for the control voltages in the frequency ranges therebelow, in that, in the case of signal portions in the non-sensible frequency range that characterize the music, the amplitude of the control voltage lying in the highest, still sensible frequency range is increased and, starting from a specific level of the signal portions, is fed to a plurality of vibration transmitters, the amplitude profile of the input signal lying in the non-sensible frequency range is impressed as an amplitude profile on an oscillation voltage lying in the sensible frequency range and this is fed as control voltage to the vibration transmitters, in that the selection amplifier used to separate the non-sensible from the sensible frequency range has a dynamic operating point setting such that the rectified output signal of the amplifier is fed back to the amplifier input in phase opposition via a time delay stage, resulting in an amplification that depends on the rate of change of the musical signal lying in the non-sensible frequency range, and in that the output signal of the amplifier thus generated is impressed as an amplitude profile on the oscillator voltage lying in the sensible range, which is subsequently used as control voltage for the vibration transmitters, in that, in the case of signal portions of the music in a non-sensible partial spectrum, said frequency range is detected in its entirety via at least two filter stages, in that, in the case of signal portions of the music in a non-sensible partial spectrum, the assignment scheme of the control voltages to the vibration transmitters is carried out with at least two filter stages such that the vibration transmitters located closer to the center line are actuated with the control voltages derived from the higher-frequency signal, and the vibration transmitters located further away from the center line are actuated with the control voltages derived from the low-frequency signal, and/or in that, with an amplitude dominance of a control voltage, further vibration transmitters are actuated with said voltage.

In the case of vibration transmitters arranged symmetrically and in pairs with respect to the center line of the belt, the vibration transmitters located directly on both sides of the center line are preferably permanently actuated with the highest-frequency control voltage of the partial spectra.

Said analog components of the electronic system can of course also be realized using functionally identical digital circuits and/or software.

In the following, essential method features are named by means of which, in the case of signal portions of the music in a non-sensible partial spectrum, these signals can also be made sensible.

The method for increasing musical sensitivity, in that vibrations derived from the audible music and correlating with the audible music are transmitted onto the skin by vibration transmitters, wherein the vibration transmitters are spatially distributed in a belt to be worn around the hips or waist and are actuated by musical signals filtered into different frequency ranges as control voltage, provides that, starting from a mean spectral width of a base spectrum from the musical spectrum, the base spectrum is divided into partial spectra, the vibration transmitters are actuated with the temporal profiles of the partial spectra, and a computationally retrievable assignment scheme exists between the frequency position of the control voltages and the position of the vibration transmitters, wherein, in the case of signal portions of the music in a non-sensible partial spectrum, the amplitude of the control voltage in the highest, still sensible partial spectrum is increased, and/or starting from a predefinable amplitude of said portions, the control voltage in the highest, still sensible partial spectrum is fed to a plurality of vibration transmitters as control voltage, and/or said frequency range is detected in its entirety via at least two filter stages, and/or the selection amplifier used to separate the non-sensible from the sensible frequency range has a dynamic operating point setting such that the rectified output signal of the amplifier is fed back to the amplifier input in phase opposition via a time delay stage, resulting in an amplification that depends on the rate of change of the musical signal lying in the non-sensible frequency range, and that the output signal of the amplifier thus generated is impressed as an amplitude profile on the oscillator voltage lying in the sensible range, which is subsequently used as control voltage for the vibration transmitters and/or in the case of signal portions of the music in a non-sensible partial spectrum and with only a very low control voltage in the highest, still sensible partial spectrum, an oscillator voltage of which the frequency lies at the sensible limit assumes the function of the control voltage.

In the case of signal portions of the music in a non-sensible partial spectrum, the assignment scheme of the control voltages to the vibration transmitters with at least two filter stages preferably provides that the vibration transmitters located closer to the center line are actuated with the control voltages derived from the higher-frequency signal, and the vibration transmitters located further away from the center line are actuated with the control voltages derived from the low-frequency signal.

In the case of an amplitude dominance of a control voltage, further vibration transmitters can be actuated with said voltage.

With regard to the explanation of these features, reference is made to the preceding statements regarding the method. They apply analogously here.

BRIEF DESCRIPTION OF THE DRAWINGS

The invention shall be explained by way of example by means of the drawings, in which:

FIG. 1 shows the device for increasing musical sensitivity (musical emotionality) in the form of a belt 12, of which only one half and the inside is shown herein—indicated by the center line 13.

DETAILED DESCRIPTION

In the depicted embodiment, seven vibration transmitters are each arranged in the belt 12 on both sides of the center line 13, preferably such that they bear against the body from hip side to hip side when the belt 12 is applied. It goes without saying that more or less vibration transmitters can also be provided.

A controller or an electronic system 14 with an interface for a music recording component 1 is integrated in the belt 12. In the case of a digital controller, the interface can also directly receive a digital input signal, preferably wirelessly, e.g. via Bluetooth. The vibration transmitters 7 are actuated by the electronic system 14. This is done in pairs and symmetrically with respect to the center line 13. It goes without saying that, instead of in pairs, the vibration transmitters 7 can also be actuated individually or in other groups of two, three or more vibration transmitters.

Figure 1:
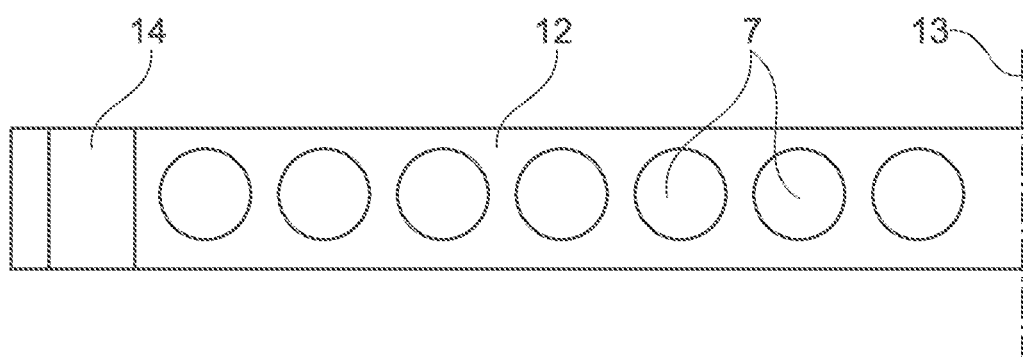
FIG. 1 shows a device with vibration transmitters in the form of a belt.
Figure 2:
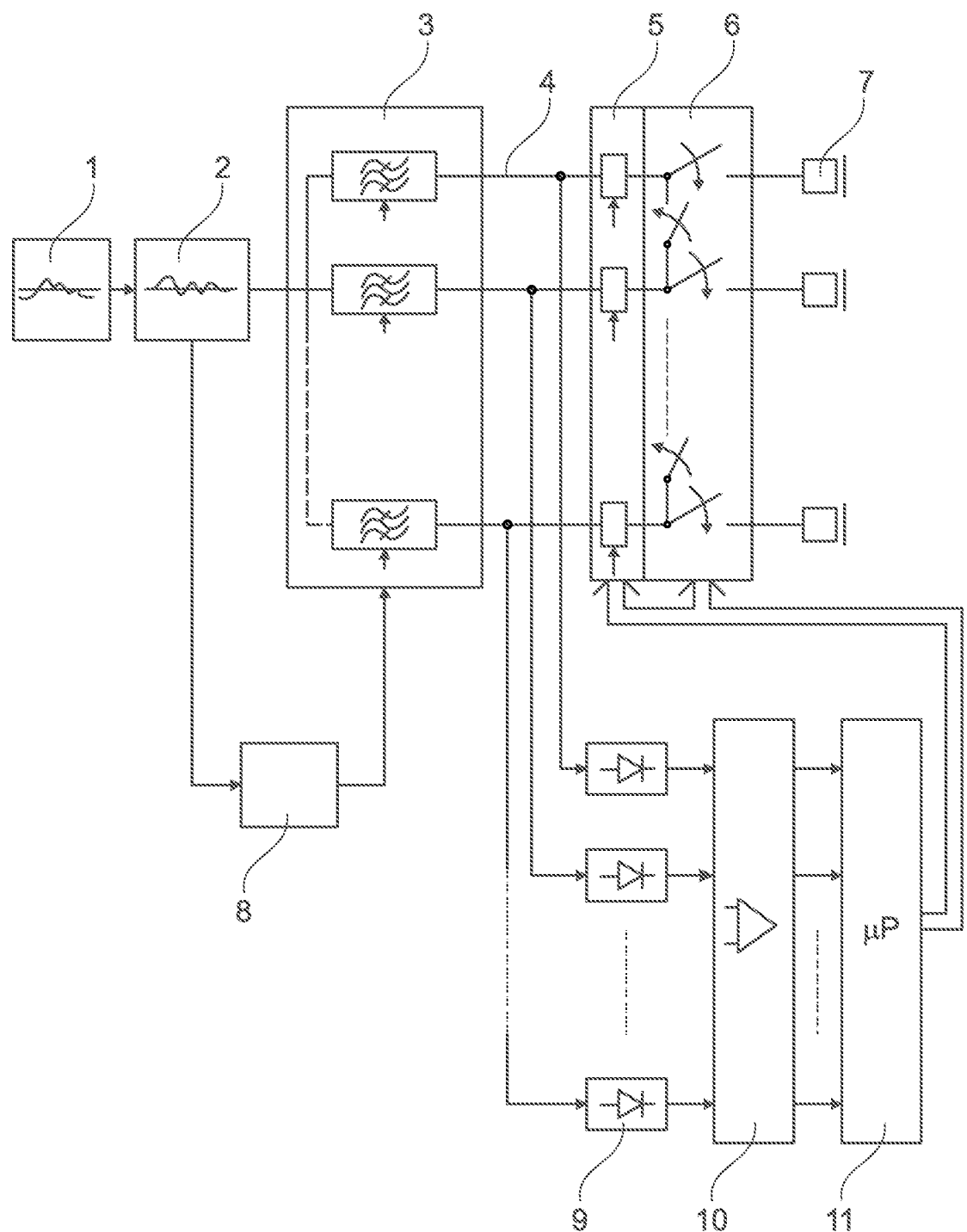
FIG. 2 shows a circuit arrangement for converting an input signal.

FIG. 2 shows the electronic system 14 for actuating the vibration transmitters 7 in the form of a circuit arrangement, by means of which vibrations derived from the audible music and correlating with the audible music are transmitted from vibration transmitters 7 onto the skin. In this case, the vibration transmitters 7 are arranged in a belt 12 to be worn around the hips or waist and are actuated by control voltages that are filtered musical signals adapted in amplitude.

The electronic system 14 consist of components that are coupled to one another in terms of circuitry, namely a music recording component 1, a circuit for deriving the base spectrum 2, controllable filter circuits 3 with a circuit 8 for adapting the filter circuits 3, circuits for amplitude detection 9, comparator circuits 10, and a digital circuit 11 for implementing the switching scheme, controllable amplifiers 5, and a switching matrix 6 for the vibration transmitters 7.

The music recording component 1 is preferably a radio component, i.e. the musical signals which the wearer of the belt 12 perceives from a loudspeaker or via headphones through the ear sensory organ are simultaneously recorded by the music recording component 1 and provided to the further components of the electronic system 14 in order to generate the control voltages for the vibration transmitters 8.

After the signal has been input into the music recording component 1, the circuit 2 derives the base spectrum, wherein, starting from a mean spectral width of a base spectrum from the musical spectrum, which can extend e.g. from 250 Hz-8 kHz, wherein the base spectrum is divided into partial spectra, the width of the base spectrum is expanded while maintaining the number of partial spectra as soon as a spectral component of the current music occurs which is outside the current base spectrum, or the width of the base spectrum is reduced while maintaining the number of partial spectra if, within a time unit, no spectral component of the current music occurs in the outer ranges of the current base spectrum.

The vibration transmitters 7 are then actuated with the filtered temporal profiles of the partial spectra, wherein there is a computationally retrievable assignment scheme between the frequency position of the control voltages and the position of the vibration transmitters 7.

The controllable filter circuits 3 do not analyze every sound, but rather the partial spectra in which the sounds lie. A frequency is thus assigned to the sounds.

The base spectrum comprises the ranges that are sensible (feelable) for the skin, e.g. from 55 Hz-93 Hz
94 Hz-160 Hz
161 Hz-280 Hz
281 Hz-460 Hz and
461 Hz-820 Hz.

and musical signal frequencies in non-sensible (non-feelable) spectra in the ranges 821 Hz-1600 Hz and
1601 Hz-3200 Hz.

In general, it can be assumed that the transition between frequencies that are sensible and non-sensible by the skin is approximately at 1000 Hz.

Parallel to the spectral division of the signals, the circuit 8 for amplitude detection of the filtered musical signals determines the amplitudes of the partial spectra in relation to their size and, in the subsequent comparator circuits, compares the size of the amplitudes.

On the basis of the determined size of the amplitudes, corresponding signals for the switching matrix 6 are generated in the digital circuit 11 for implementing the preprogrammed switching scheme and thus for activating the vibration transmitters 7.

The switching matrix 6 is designed such that any of the vibration transmitters 7 and also combinations of vibration transmitters 7 can be activated with the control voltages from the filter circuit 3.

The proposed method does not generate a new signal that can be converted by means of the vibration transmitters 7, but instead, the filtered and amplitude-adapted musical signal is transmitted directly, wherein it is determined by the electronic system 14 which vibration transmitter 7 is actuated. The most essential actuations are disclosed in detail in the methods.

As high a correlation as possible between heard and felt perceptions can be achieved by the direct conversion of the musical signal into vibrations, the local impact distribution of the filtered musical signals, the emphasis of the dominant musical signals by expanding the extent of the impact, the transfer of the signal portions in the non-sensible range into the sensible range, and the variable base spectrum adapting to the current musical spectrum.

The invention claimed is:

1. A method for increasing perception of acoustic events, in particular for increasing musical sensitivity, the method comprising:
   transmitting vibrations derived from an acoustic event and correlated with the acoustic event onto the skin of a person by vibration transmitters, wherein the vibration transmitters are spatially distributed on the skin;
   determining control voltages, by a controller to which an input signal reproducing the acoustic event is fed, and actuating the vibration transmitters each with one of the determined control voltages to generate a vibration that is sensible on the skin, wherein an amplitude profile of the input signal is in a non-sensible frequency range and is impressed as an amplitude profile on an oscillation voltage in a sensible frequency range;
   determining a base spectrum from the frequency spectrum of the acoustic event, wherein the base spectrum is divided into partial spectra which each comprise a frequency range of the base spectrum, wherein the control voltages are each derived from the frequency range of at least one assigned partial spectrum, and wherein frequency positions of the control voltages and/or the partial spectra are assigned to positions of the vibration transmitters; and
   separating, by a selection amplifier, the non-sensible frequency range from the sensible frequency range, wherein the selection amplifier has a dynamic operating point setting such that,
      a rectified output signal of the selection amplifier is fed back to the amplifier input in phase opposition via a time delay stage, resulting in an amplification that depends on a rate of change of the input signal in the non-sensible frequency range, and
      an amplitude profile of the rectified output signal of the amplifier is impressed as an amplitude profile on an oscillator voltage in the sensible range and used as the control voltages for the vibration transmitters.

2. The method according to claim 1, wherein the determination of the base spectrum comprises an expansion and/or reduction of the width of the base spectrum while maintaining the number of partial spectra,
   wherein the width of the base spectrum is reduced if, within a time unit, a number of spectral components occurs in the frequency range of the acoustic event in the edge regions of the current base spectrum which lies below a specified threshold value, in particular no spectral component,
   wherein the width of the base spectrum is expanded if a spectral component which lies outside the selected base spectrum occurs in the frequency spectrum of the acoustic event.

3. The method according to claim 1, wherein the number of vibration transmitters actuated by a control voltage depends on the amplitude ratio of the individual control voltages,
   wherein, if the amplitude of the control voltages of all partial spectra is the same or substantially the same, the control voltages are fed to the vibration transmitters in the sequence of their frequency position and/or
   wherein, when a predetermined deviation between the amplitudes of the control voltages is reached, the dominant control voltage is fed to the vibration transmitter of the associated partial spectrum and one or more vibration transmitters of partial spectra with a higher frequency position.

4. The method according to claim 1, wherein at least one of the vibration transmitters is permanently actuated with the highest frequency control voltage.

5. The method according to claim 1, wherein the control voltage which has the highest amplitude in the frequency position below the control voltage with the maximum value is also used to actuate one or more vibration transmitters which lie between said two control voltages, and there is a corresponding assignment for the control voltages in the frequency ranges therebelow.

6. The method according to claim 1, wherein the vibration transmitters are arranged so as to be distributed on the skin in an arrangement extending in a distribution direction, wherein the vibration transmitters are preferably arranged symmetrically and in pairs with respect to a center line of the arrangement and are actuated in pairs or individually, wherein the frequency of the control voltages further preferably increases in the direction of the center line.

7. The method according to claim 6, wherein at least the vibration transmitters located directly on both sides of the center line are permanently actuated with the highest frequency control voltage.

8. The method according to claim 1, wherein the amplitude of the control voltage in the highest, still sensible partial spectrum is increased if signal portions of the input signal occur in a non-sensible partial spectrum.

9. The method according to claim 1, wherein, if signal portions of the input signal occur in a non-sensible partial spectrum, the control voltage in the highest, still sensible partial spectrum, starting from a predefined amplitude of said signal portions, is fed to a plurality of vibration transmitters as control voltage.

10. The method according to claim 1, wherein, in the case of signal portions of the input signal being in a non-sensible partial spectrum, the frequency range of said partial spectrum is detected in its entirety via one or more, preferably at least two, filter stages.

11. The method according to claim 10, wherein, if signal portions of the input signal are in a non-sensible partial spectrum, the control voltages are assigned to the vibration transmitters with one or more, preferably at least two, filter stages such that vibration transmitters arranged closer to the center line are actuated with the control voltages derived from a higher-frequency signal portion, and vibration transmitters located further away from the center line are actuated with the control voltages derived from a low-frequency signal portion.

12. The method according to claim 11, wherein, in the case of an amplitude dominance of a control voltage, at least one further vibration transmitter, in particular a vibration transmitter adjacent to the assigned vibration transmitter, is actuated with said control voltage in addition to the assigned vibration transmitter.

13. The method according to claim 1, wherein, in the case of acoustic events with a limited spectral range, the division of the partial spectra for the control voltages is spread according to the total width of the frequency spectrum.

14. The method according to claim 1, wherein control commands for changing a programming and/or the assignment can be transmitted via a user interface, preferably via software.

15. A device for increasing perception of acoustic events, which is configured to carry out the method of claim 1, wherein the device has a plurality of vibration transmitters for transmitting vibrations onto the skin of a person and a controller connected to the vibration transmitters for actuating the vibration transmitters with a control voltage in order to generate the vibrations,
wherein the vibration transmitters are arranged at positions in a predetermined arrangement such that they can be spatially distributed on the skin of the person,
wherein the device is configured to transmit vibrations derived from an acoustic event and correlating with the acoustic event onto the skin of a person by means of the vibration transmitters, and
wherein the controller is configured to receive an input signal belonging to the acoustic event, to determine control voltages and to actuate the vibration transmitters with one of the determined control voltages in order to generate a vibration that is sensible on the skin.

16. The device according to claim 15, wherein the vibration transmitters are arranged in an arrangement extending in a distribution direction, preferably symmetrically and in pairs with respect to a center line of the arrangement, and can be actuated in pairs or individually.

17. The device according to claim 15, wherein the device is designed as a belt to be worn around the hips, as a band or as an item of clothing, preferably such that, when used, the vibration transmitters can be placed on the skin in the area of the abdomen and the hips of the person.

18. The device according to claim 15, wherein the vibration transmitters are arranged such that they come into contact with the skin of the person when said person wears the device or are arranged relative to the skin of the person such that a vibration can be transmitted onto the skin.

19. The device according to claim 15, wherein the controller for receiving the input signal has at least one interface, in particular a wireless interface, and/or a music recording device for recording sound waves of the acoustic event.

20. The device according to claim 15, wherein the controller comprises a digital controller and/or software.

21. The device according to claim 15, wherein the controller comprises an electronic system consisting of components that are coupled to one another in terms of circuitry, wherein the components comprise a music recording component, a circuit for determining the base spectrum, controllable filter circuits with a circuit for adapting the filter circuits and circuits for amplitude detection, and preferably comparator circuits, a digital circuit, controllable amplifiers and a switching matrix.

* * * * *